United States Patent
Bathe et al.

(10) Patent No.: US 7,105,302 B2
(45) Date of Patent: Sep. 12, 2006

(54) NUCLEOTIDE SEQUENCES CODING FOR THE PKNB GENE

(75) Inventors: Brigitte Bathe, Saltzkotten (DE); Stephan Hans, Osnabrueck (DE); Mike Farwick, Bielefeld (DE); Thomas Hermann, Bielefeld (DE)

(73) Assignee: Degussa AG, Duesseldorf (DE)

( * ) Notice: Subject to any disclaimer, the term of this patent is extended or adjusted under 35 U.S.C. 154(b) by 35 days.

(21) Appl. No.: 10/940,606

(22) Filed: Sep. 15, 2004

(65) Prior Publication Data

US 2005/0130277 A1 Jun. 16, 2005

Related U.S. Application Data

(62) Division of application No. 09/949,970, filed on Sep. 12, 2001, now Pat. No. 6,939,692.

(60) Provisional application No. 60/297,250, filed on Jun. 12, 2001.

(30) Foreign Application Priority Data

Sep. 12, 2000 (DE) ................. 100 44 912
Apr. 25, 2001 (DE) ................. 101 20 095

(51) Int. Cl.
*C12Q 1/68* (2006.01)
*C12N 9/12* (2006.01)
*C12N 1/20* (2006.01)
*C12N 15/09* (2006.01)
*C07H 21/04* (2006.01)

(52) U.S. Cl. ............... 435/6; 435/4; 435/106; 435/183; 435/193; 435/194; 435/252.3; 435/252.32; 435/320.1; 536/23.2

(58) Field of Classification Search ............. 435/106, 435/183, 193, 194, 252.3, 252.32, 320.1, 435/4, 6; 536/23.2
See application file for complete search history.

(56) References Cited

U.S. PATENT DOCUMENTS 6,962,989 B1 * 11/2005 Pompejus et al. ......... 536/23.7

FOREIGN PATENT DOCUMENTS

EP  1 029 919  8/2000
EP  1 108 790  6/2001

OTHER PUBLICATIONS

Fabbro et al. Protein Expr Purif. Oct. 1999;17(1):83-8.*
Database Swall "Online", EBI, "M. Leprae PknB", XP 002185694, Acc. No. P54744, Oct. 1, 1996.
Josef Cremer, et al., Applied and Environmental Microbiology, vol. 57, No. 6, pp. 1746-1752, "Control of the Lysine Biosynthesis Sequence in Corynebacterium Glutamicum as Analyzed by Overexpression of the Individual Corresponding Genes", Jun. 1, 1991.
Cocito et al. Accession No. AAZ38383, Feb. 22, 2000 (Alignment No. 1).
Cocito et al, Accession AAZ38383, Feb. 22, 2000 (Alignment No. 2).
Zhao et al, Accession AQ391796, Mar. 6, 1999.
Attwood et al, Which craft is best in bioinformatics? Comput. Chem. 2001, vol. 25(4), pp. 329-339.
Ponting, C.P. Issues in predicting protein function from sequence. Brief. Bioinform, Mar. 2001, vol. 2(1), pp. 19-29.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

An isolated polynucleotide which contains a polynucleotide sequence selected from the group comprising:
(a) a polynucleotide which is at least 70% identical to a polynucleotide coding for a polypeptide containing the amino acid sequence of SEQ ID No. 2,
(b) a polynucleotide coding for a polypeptide containing an amino acid sequence which is at least 70% identical to the amino acid sequence of SEQ ID No. 2,
(c) a polynucleotide which is complementary to the polynucleotides of (a) or (b), and
(d) a polynucleotide containing at least 15 consecutive nucleotides of the polynucleotide sequence of (a), (b) or (c), and a fermentation process for the preparation of L-amino acids using corynebacteria in which at least the pknB gene is amplified, and to the use, as hybridization probes, of polynucleotides containing the sequences according to the invention.

4 Claims, No Drawings

SEQUENCE LISTING

```
<160> NUMBER OF SEQ ID NOS: 4

<210> SEQ ID NO 1
<211> LENGTH: 2875
<212> TYPE: DNA
<213> ORGANISM: Corynebacterium glutamicum
<220> FEATURE:
<221> NAME/KEY: CDS
<222> LOCATION: (594)..(2474)
<223> OTHER INFORMATION:

<400> SEQUENCE: 1
cgcacgagcg cgatgatggc gcaggcggag gcgccgtcgc caagcgaatc aacggcgatg      60
ctgggcaggg tggcccggcc tgcaacaatc acccaagaag cggccccgaa acgcggttcc     120
ggcattggca ttggtctgtt catcgcagct ttgcttgccg tgattattgg cgcggtgatc     180
tatgcgggca ccaccggaat tttgttcaac gacactccgg aagaaaccac cacacctgaa     240
```

-continued

```
accattacgg aaacatacac cccaaccgtg gaggaaacca cctctcagtg ggtaccgcca    300
acgcctccaa cacggtcaac attcaccgaa cctgaaacaa cttcacaccg tccgacgaca    360
agtgaagaga gcacatccga ggaaccaacc acggaagctc caacaagtag ccgaactgtg    420
cctcaaatcc ctacctctac acctaggacg agtgctagcg ttccagttga gactaatgca    480
ccggctgatg atttaatcga cgccgtaaat ggcctattgg atgtaggagg agcgcagtga    540
ccttcgtgat cgctgatcgc tatgaactgg atgccgtcat cggctccggt ggc atg      596
                                                            Met
                                                            1 agc gag gtg ttc gcg gcc acc gac acg ctc att ggt cgg gag gtc gcg    644
Ser Glu Val Phe Ala Ala Thr Asp Thr Leu Ile Gly Arg Glu Val Ala
            5                   10                  15 gta aag atg ctg cgc atc gac ctt gcg aaa gat ccc aat ttc cga gaa    692
Val Lys Met Leu Arg Ile Asp Leu Ala Lys Asp Pro Asn Phe Arg Glu
        20                  25                  30 cgc ttc cgc agg gaa gcc caa aac tcc gga agg ttg agc cac tct tcg    740
Arg Phe Arg Arg Glu Ala Gln Asn Ser Gly Arg Leu Ser His Ser Ser
    35                  40                  45 atc gtc gct gtt ttt gac acc ggc gaa gta gac aaa gac ggc acc tct    788
Ile Val Ala Val Phe Asp Thr Gly Glu Val Asp Lys Asp Gly Thr Ser
50                  55                  60                  65 gtt ccc tac att gtg atg gaa cgc gtg cag ggt cga aac ctg cgc gaa    836
Val Pro Tyr Ile Val Met Glu Arg Val Gln Gly Arg Asn Leu Arg Glu
                70                  75                  80 gtt gtc acc gaa gac ggc gta ttc acc cca gtt gag gca gcc aac atc    884
Val Val Thr Glu Asp Gly Val Phe Thr Pro Val Glu Ala Ala Asn Ile
            85                  90                  95 ctc atc cct gtg tgt gaa gcg ctg cag gca tcc cat gac gcc ggc att    932
Leu Ile Pro Val Cys Glu Ala Leu Gln Ala Ser His Asp Ala Gly Ile
        100                 105                 110 att cac cgc gat gtg aaa ccc gcc aac atc atg atc acc aac acc ggt    980
Ile His Arg Asp Val Lys Pro Ala Asn Ile Met Ile Thr Asn Thr Gly
    115                 120                 125 ggc gtg aaa gtc atg gac ttc ggc atc gcc cgc gcg gtc aac gat tcc   1028
Gly Val Lys Val Met Asp Phe Gly Ile Ala Arg Ala Val Asn Asp Ser
130                 135                 140                 145 acc tcc gcc atg act caa acc tcc gca gtc atc ggc acc gcc cag tac   1076
Thr Ser Ala Met Thr Gln Thr Ser Ala Val Ile Gly Thr Ala Gln Tyr
                150                 155                 160 ctc tcc cct gag cag gcc cgc ggc aaa ccc gcc gat gcg cgt tcc gat   1124
Leu Ser Pro Glu Gln Ala Arg Gly Lys Pro Ala Asp Ala Arg Ser Asp
            165                 170                 175 att tac gcc acc ggc tgc gtc atg tac gaa tta gtc acc ggt aag cca   1172
Ile Tyr Ala Thr Gly Cys Val Met Tyr Glu Leu Val Thr Gly Lys Pro
        180                 185                 190 cct ttt gaa ggc gag tcc cct ttc gcc gtg gcc tac caa cac gtc cag   1220
Pro Phe Glu Gly Glu Ser Pro Phe Ala Val Ala Tyr Gln His Val Gln
    195                 200                 205 gaa gac ccc acc cct cct tcg gat ttc atc gcg gac ctc acc ccg acc   1268
Glu Asp Pro Thr Pro Pro Ser Asp Phe Ile Ala Asp Leu Thr Pro Thr
210                 215                 220                 225 tct gct gtc aac gtg gat gcc gtg gta ctc acc gcc atg gca aaa cac   1316
Ser Ala Val Asn Val Asp Ala Val Val Leu Thr Ala Met Ala Lys His
                230                 235                 240 ccc gcc gac cgc tac caa aca gcc tcc gaa atg gcc gct gac ctg ggc   1364
Pro Ala Asp Arg Tyr Gln Thr Ala Ser Glu Met Ala Ala Asp Leu Gly
            245                 250                 255
```

```
cgg cta tcc cgc aat gca gtc tcc cat gcc gca cgc gcg cat gta gaa    1412
Arg Leu Ser Arg Asn Ala Val Ser His Ala Ala Arg Ala His Val Glu
        260                 265                 270 aca gaa gaa acc cca gaa gag ccc gaa act cgc ttc tcg acg cgc acc    1460
Thr Glu Glu Thr Pro Glu Glu Pro Glu Thr Arg Phe Ser Thr Arg Thr
275                 280                 285 tcc acc caa gtg gcc ccc gcc gca ggc gtg gct gcg gcc agt acg ggg    1508
Ser Thr Gln Val Ala Pro Ala Ala Gly Val Ala Ala Ala Ser Thr Gly
290                 295                 300                 305 tca ggg tct tct tcg cgt aaa cgt gga tcc aga ggc ctc acc gcc ctg    1556
Ser Gly Ser Ser Ser Arg Lys Arg Gly Ser Arg Gly Leu Thr Ala Leu
        310                 315                 320 gcc atc gtg tta tcc cta ggt gtc gtc ggc gtt gcc ggt gcc ttc acc    1604
Ala Ile Val Leu Ser Leu Gly Val Val Gly Val Ala Gly Ala Phe Thr
        325                 330                 335 tac gac tac ttt gcc aac agc tcc tcc act gca acc agc gcg atc ccc    1652
Tyr Asp Tyr Phe Ala Asn Ser Ser Ser Thr Ala Thr Ser Ala Ile Pro
        340                 345                 350 aat gtg gaa ggc ctc ccg cag caa gaa gct ctc aca gaa ctt caa gca    1700
Asn Val Glu Gly Leu Pro Gln Gln Glu Ala Leu Thr Glu Leu Gln Ala
355                 360                 365 gca gga ttt gtt gtc aac atc gtc gaa gaa gcc agc gcc gac gtc gcc    1748
Ala Gly Phe Val Val Asn Ile Val Glu Glu Ala Ser Ala Asp Val Ala
370                 375                 380                 385 gaa ggc ctc gtc atc cga gca aac cca agc gtt gga tcc gaa atc cgc    1796
Glu Gly Leu Val Ile Arg Ala Asn Pro Ser Val Gly Ser Glu Ile Arg
                390                 395                 400 caa ggg gcc acc gtc acc atc acc gtg tcc acc ggc cga gaa atg atc    1844
Gln Gly Ala Thr Val Thr Ile Thr Val Ser Thr Gly Arg Glu Met Ile
        405                 410                 415 aac atc cca gac gtc tcc ggc atg aca ctt gag gac gcc gcc cgc gcc    1892
Asn Ile Pro Asp Val Ser Gly Met Thr Leu Glu Asp Ala Ala Arg Ala
        420                 425                 430 ctc gaa gac gtt ggt ctc ata ctc aac caa aac gtt cgg gaa gaa acc    1940
Leu Glu Asp Val Gly Leu Ile Leu Asn Gln Asn Val Arg Glu Glu Thr
435                 440                 445 tcc gac gac gtc gaa tct ggc ctc gtc atc gac caa aac ccc gaa gcc    1988
Ser Asp Asp Val Glu Ser Gly Leu Val Ile Asp Gln Asn Pro Glu Ala
450                 455                 460                 465 ggc caa gaa gta gtc gtg ggt tcc tct gta tct cta acc atg tct tca    2036
Gly Gln Glu Val Val Val Gly Ser Ser Val Ser Leu Thr Met Ser Ser
                470                 475                 480 ggc acc gag agc atc cga gtg ccc aac ctc acc ggc atg aac tgg tca    2084
Gly Thr Glu Ser Ile Arg Val Pro Asn Leu Thr Gly Met Asn Trp Ser
        485                 490                 495 caa gca gaa caa aac ctc atc tcc atg ggc ttt aac ccc aca gct tcc    2132
Gln Ala Glu Gln Asn Leu Ile Ser Met Gly Phe Asn Pro Thr Ala Ser
        500                 505                 510 tac tta gac agc agc gaa cca gaa ggc gaa gtc ctc tca gtt tcc agc    2180
Tyr Leu Asp Ser Ser Glu Pro Glu Gly Glu Val Leu Ser Val Ser Ser
        515                 520                 525 caa gga act gaa cta ccc aag ggt tca tcc atc aca gtg gaa gtc tcc    2228
Gln Gly Thr Glu Leu Pro Lys Gly Ser Ser Ile Thr Val Glu Val Ser
530                 535                 540                 545 aac ggc atg ctc atc caa gcc ccc gat ctc gcc cgc atg tcc acc gaa    2276
Asn Gly Met Leu Ile Gln Ala Pro Asp Leu Ala Arg Met Ser Thr Glu
                550                 555                 560 cag gcc atc agt gcc ctc cgc gct gct ggc tgg acc gcc cca gat caa    2324
Gln Ala Ile Ser Ala Leu Arg Ala Ala Gly Trp Thr Ala Pro Asp Gln
        565                 570                 575
```

-continued

```
tcc ctg atc gtc ggc gac ccc atc cac acc gca gcc ctc gtg gat caa    2372
Ser Leu Ile Val Gly Asp Pro Ile His Thr Ala Ala Leu Val Asp Gln
        580                 585                 590 aac aaa atc gga ttc caa tcc cca acc cct gca acc ctc ttc cgc aaa    2420
Asn Lys Ile Gly Phe Gln Ser Pro Thr Pro Ala Thr Leu Phe Arg Lys
    595                 600                 605 gac gcc caa gtg caa gtg cga ctc ttc gaa ttc gat ctc gct gca ctc    2468
Asp Ala Gln Val Gln Val Arg Leu Phe Glu Phe Asp Leu Ala Ala Leu
610                 615                 620                 625 gtg caa tagccaacaa ggaaaccgtc aaggtagctg cccggcaac tgatacgtta      2524
Val Gln agctcaaaca agataagtac cagttgctgg ggttttcca agacaataaa ttatgaaggt   2584
gtgaacaatg ccaaaggcaa gagtaactaa aaacgagacc gcaccggttt caagcaaccc  2644
aagcgcaaac cgcaccccgg ttaagatcaa ttccgccgga accccaatgt ggtacaaggt  2704
catcatgttt gccttcatga tcgtcggcct agcctggttg atcattaact acctcgtggg  2764
cccacagatc ccattcatgg ctgatcttgg tgcatggaac tatggcatcg gcttcggtct  2824
gatgatcatc ggcctactca tgaccatggg ttggcgttaa tccttcaaaa a           2875
```

<210> SEQ ID NO 2
<211> LENGTH: 627
<212> TYPE: PRT
<213> ORGANISM: Corynebacterium glutamicum

<400> SEQUENCE: 2

```
Met Ser Glu Val Phe Ala Ala Thr Asp Thr Leu Ile Gly Arg Glu Val
1               5                   10                  15

Ala Val Lys Met Leu Arg Ile Asp Leu Ala Lys Asp Pro Asn Phe Arg
            20                  25                  30

Glu Arg Phe Arg Arg Glu Ala Gln Asn Ser Gly Arg Leu Ser His Ser
        35                  40                  45

Ser Ile Val Ala Val Phe Asp Thr Gly Glu Val Asp Lys Asp Gly Thr
    50                  55                  60

Ser Val Pro Tyr Ile Val Met Glu Arg Val Gln Gly Arg Asn Leu Arg
65                  70                  75                  80

Glu Val Val Thr Glu Asp Gly Val Phe Thr Pro Val Glu Ala Ala Asn
                85                  90                  95

Ile Leu Ile Pro Val Cys Glu Ala Leu Gln Ala Ser His Asp Ala Gly
            100                 105                 110

Ile Ile His Arg Asp Val Lys Pro Ala Asn Ile Met Ile Thr Asn Thr
        115                 120                 125

Gly Gly Val Lys Val Met Asp Phe Gly Ile Ala Arg Ala Val Asn Asp
    130                 135                 140

Ser Thr Ser Ala Met Thr Gln Thr Ser Ala Val Ile Gly Thr Ala Gln
145                 150                 155                 160

Tyr Leu Ser Pro Glu Gln Ala Arg Gly Lys Pro Ala Asp Ala Arg Ser
                165                 170                 175

Asp Ile Tyr Ala Thr Gly Cys Val Met Tyr Glu Leu Val Thr Gly Lys
            180                 185                 190

Pro Pro Phe Glu Gly Glu Ser Pro Phe Ala Val Ala Tyr Gln His Val
        195                 200                 205

Gln Glu Asp Pro Thr Pro Pro Ser Asp Phe Ile Ala Asp Leu Thr Pro
    210                 215                 220

Thr Ser Ala Val Asn Val Asp Ala Val Val Leu Thr Ala Met Ala Lys
```

```
            225                 230                 235                 240

His Pro Ala Asp Arg Tyr Gln Thr Ala Ser Glu Met Ala Ala Asp Leu
                245                 250                 255

Gly Arg Leu Ser Arg Asn Ala Val Ser His Ala Ala Arg Ala His Val
                260                 265                 270

Glu Thr Glu Thr Pro Glu Pro Glu Thr Arg Phe Ser Thr Arg
                275                 280                 285

Thr Ser Thr Gln Val Ala Pro Ala Ala Gly Val Ala Ala Ala Ser Thr
                290                 295                 300

Gly Ser Gly Ser Ser Arg Lys Arg Gly Ser Arg Gly Leu Thr Ala
305                 310                 315                 320

Leu Ala Ile Val Leu Ser Leu Gly Val Val Gly Val Ala Gly Ala Phe
                325                 330                 335

Thr Tyr Asp Tyr Phe Ala Asn Ser Ser Thr Ala Thr Ser Ala Ile
                340                 345                 350

Pro Asn Val Glu Gly Leu Pro Gln Gln Glu Ala Leu Thr Glu Leu Gln
                355                 360                 365

Ala Ala Gly Phe Val Val Asn Ile Val Glu Glu Ala Ser Ala Asp Val
                370                 375                 380

Ala Glu Gly Leu Val Ile Arg Ala Asn Pro Ser Val Gly Ser Glu Ile
385                 390                 395                 400

Arg Gln Gly Ala Thr Val Thr Ile Thr Val Ser Thr Gly Arg Glu Met
                405                 410                 415

Ile Asn Ile Pro Asp Val Ser Gly Met Thr Leu Glu Asp Ala Ala Arg
                420                 425                 430

Ala Leu Glu Asp Val Gly Leu Ile Leu Asn Gln Asn Val Arg Glu Glu
                435                 440                 445

Thr Ser Asp Asp Val Glu Ser Gly Leu Val Ile Asp Gln Asn Pro Glu
                450                 455                 460

Ala Gly Gln Glu Val Val Val Gly Ser Ser Val Ser Leu Thr Met Ser
465                 470                 475                 480

Ser Gly Thr Glu Ser Ile Arg Val Pro Asn Leu Thr Gly Met Asn Trp
                485                 490                 495

Ser Gln Ala Glu Gln Asn Leu Ile Ser Met Gly Phe Asn Pro Thr Ala
                500                 505                 510

Ser Tyr Leu Asp Ser Ser Glu Pro Glu Gly Glu Val Leu Ser Val Ser
                515                 520                 525

Ser Gln Gly Thr Glu Leu Pro Lys Gly Ser Ser Ile Thr Val Glu Val
                530                 535                 540

Ser Asn Gly Met Leu Ile Gln Ala Pro Asp Leu Ala Arg Met Ser Thr
545                 550                 555                 560

Glu Gln Ala Ile Ser Ala Leu Arg Ala Ala Gly Trp Thr Ala Pro Asp
                565                 570                 575

Gln Ser Leu Ile Val Gly Asp Pro Ile His Thr Ala Ala Leu Val Asp
                580                 585                 590

Gln Asn Lys Ile Gly Phe Gln Ser Pro Thr Pro Ala Thr Leu Phe Arg
                595                 600                 605

Lys Asp Ala Gln Val Gln Val Arg Leu Phe Glu Phe Asp Leu Ala Ala
        610                 615                 620

Leu Val Gln
625

<210> SEQ ID NO 3
```

-continued

```
<211> LENGTH: 2875
<212> TYPE: DNA
<213> ORGANISM: Corynebacterium glutamicum
<220> FEATURE:
<221> NAME/KEY: CDS
<222> LOCATION: (594)..(2474)
<223> OTHER INFORMATION:
<220> FEATURE:
<221> NAME/KEY: misc_feature
<222> LOCATION: (2343)..(2343)
<223> OTHER INFORMATION: C-T transition

<400> SEQUENCE: 3
```

| | |
|---|---|
| cgcacgagcg cgatgatggc gcaggcggag gcgccgtcgc caagcgaatc aacggcgatg | 60 |
| ctgggcaggg tggcccggcc tgcaacaatc acccaagaag cggccccgaa acgcggttcc | 120 |
| ggcattggca ttggtctgtt catcgcagct ttgcttgccg tgattattgg cgcggtgatc | 180 |
| tatgcgggca ccaccggaat tttgttcaac gacactccgg aagaaaccac cacacctgaa | 240 |
| accattacga aacatacac cccaaccgtg gaggaaacca cctctcagtg ggtaccgcca | 300 |
| acgcctccaa cacggtcaac attcaccgaa cctgaaacaa cttcacaccg tccgacgaca | 360 |
| agtgaagaga gcacatccga ggaaccaacc acggaagctc aacaagtag ccgaactgtg | 420 |
| cctcaaatcc ctacctctac acctaggacg agtgctagcg ttccagttga gactaatgca | 480 |
| ccggctgatg atttaatcga cgccgtaaat ggcctattgg atgtaggagg agcgcagtga | 540 |
| ccttcgtgat cgctgatcgc tatgaactgg atgccgtcat cggctccggt ggc atg | 596 |
| | Met |
| | 1 |

| agc gag gtg ttc gcg gcc acc gac acg ctc att ggt cgg gag gtc gcg | 644 |
|---|---|
| Ser Glu Val Phe Ala Ala Thr Asp Thr Leu Ile Gly Arg Glu Val Ala | |
| 5 10 15 | |

| gta aag atg ctg cgc atc gac ctt gcg aaa gat ccc aat ttc cga gaa | 692 |
|---|---|
| Val Lys Met Leu Arg Ile Asp Leu Ala Lys Asp Pro Asn Phe Arg Glu | |
| 20 25 30 | |

| cgc ttc cgc agg gaa gcc caa aac tcc gga agg ttg agc cac tct tcg | 740 |
|---|---|
| Arg Phe Arg Arg Glu Ala Gln Asn Ser Gly Arg Leu Ser His Ser Ser | |
| 35 40 45 | |

| atc gtc gct gtt ttt gac acc ggc gaa gta gac aaa gac ggc acc tct | 788 |
|---|---|
| Ile Val Ala Val Phe Asp Thr Gly Glu Val Asp Lys Asp Gly Thr Ser | |
| 50 55 60 65 | |

| gtt ccc tac att gtg atg gaa cgc gtg cag ggt cga aac ctg cgc gaa | 836 |
|---|---|
| Val Pro Tyr Ile Val Met Glu Arg Val Gln Gly Arg Asn Leu Arg Glu | |
| 70 75 80 | |

| gtt gtc acc gaa gac ggc gta ttc acc cca gtt gag gca gcc aac atc | 884 |
|---|---|
| Val Val Thr Glu Asp Gly Val Phe Thr Pro Val Glu Ala Ala Asn Ile | |
| 85 90 95 | |

| ctc atc cct gtg tgt gaa gcg ctg cag gca tcc cat gac gcc ggc att | 932 |
|---|---|
| Leu Ile Pro Val Cys Glu Ala Leu Gln Ala Ser His Asp Ala Gly Ile | |
| 100 105 110 | |

| att cac cgc gat gtg aaa ccc gcc aac atc atg atc acc aac acc ggt | 980 |
|---|---|
| Ile His Arg Asp Val Lys Pro Ala Asn Ile Met Ile Thr Asn Thr Gly | |
| 115 120 125 | |

| ggc gtg aaa gtc atg gac ttc ggc atc gcc cgc gcg gtc aac gat tcc | 1028 |
|---|---|
| Gly Val Lys Val Met Asp Phe Gly Ile Ala Arg Ala Val Asn Asp Ser | |
| 130 135 140 145 | |

| acc tcc gcc atg act caa acc tcc gca gtc atc ggc acc gcc cag tac | 1076 |
|---|---|
| Thr Ser Ala Met Thr Gln Thr Ser Ala Val Ile Gly Thr Ala Gln Tyr | |
| 150 155 160 | |

| ctc tcc cct gag cag gcc cgc ggc aaa ccc gcc gat gcg cgt tcc gat | 1124 |
|---|---|
| Leu Ser Pro Glu Gln Ala Arg Gly Lys Pro Ala Asp Ala Arg Ser Asp | |
| 165 170 175 | |

-continued

| | |
|---|---|
| att tac gcc acc ggc tgc gtc atg tac gaa tta gtc acc ggt aag cca<br>Ile Tyr Ala Thr Gly Cys Val Met Tyr Glu Leu Val Thr Gly Lys Pro<br>    180                             185                        190 | 1172 |
| cct ttt gaa ggc gag tcc cct ttc gcc gtg gcc tac caa cac gtc cag<br>Pro Phe Glu Gly Glu Ser Pro Phe Ala Val Ala Tyr Gln His Val Gln<br>195                             200                        205 | 1220 |
| gaa gac ccc acc cct cct tcg gat ttc atc gcg gac ctc acc ccg acc<br>Glu Asp Pro Thr Pro Pro Ser Asp Phe Ile Ala Asp Leu Thr Pro Thr<br>210                           215                      220               225 | 1268 |
| tct gct gtc aac gtg gat gcc gta ctc acc gcc atg gca aaa cac<br>Ser Ala Val Asn Val Asp Ala Val Val Leu Thr Ala Met Ala Lys His<br>                    230                   235                 240 | 1316 |
| ccc gcc gac cgc tac caa aca gcc tcc gaa atg gcc gct gac ctg ggc<br>Pro Ala Asp Arg Tyr Gln Thr Ala Ser Glu Met Ala Ala Asp Leu Gly<br>         245                      250                       255 | 1364 |
| cgg cta tcc cgc aat gca gtc tcc cat gcc gca cgc gcg cat gta gaa<br>Arg Leu Ser Arg Asn Ala Val Ser His Ala Ala Arg Ala His Val Glu<br>        260                       265                    270 | 1412 |
| aca gaa gaa acc cca gaa gag ccc gaa act cgc ttc tcg acg cgc acc<br>Thr Glu Glu Thr Pro Glu Glu Pro Glu Thr Arg Phe Ser Thr Arg Thr<br>275                           280                       285 | 1460 |
| tcc acc caa gtg gcc ccc gcc gca ggc gtg gct gcg gcc agt acg ggg<br>Ser Thr Gln Val Ala Pro Ala Ala Gly Val Ala Ala Ala Ser Thr Gly<br>290                           295                       300               305 | 1508 |
| tca ggg tct tct tcg cgt aaa cgt gga tcc aga ggc ctc acc gcc ctg<br>Ser Gly Ser Ser Ser Arg Lys Arg Gly Ser Arg Gly Leu Thr Ala Leu<br>                 310                     315                 320 | 1556 |
| gcc atc gtg tta tcc cta ggt gtc gtc ggc gtt gcc ggt gcc ttc acc<br>Ala Ile Val Leu Ser Leu Gly Val Val Gly Val Ala Gly Ala Phe Thr<br>                    325                   330                    335 | 1604 |
| tac gac tac ttt gcc aac agc tcc tcc act gca acc agc gcg atc ccc<br>Tyr Asp Tyr Phe Ala Asn Ser Ser Ser Thr Ala Thr Ser Ala Ile Pro<br>       340                       345                       350 | 1652 |
| aat gtg gaa ggc ctc ccg cag caa gaa gct ctc aca gaa ctt caa gca<br>Asn Val Glu Gly Leu Pro Gln Gln Glu Ala Leu Thr Glu Leu Gln Ala<br>355                           360                       365 | 1700 |
| gca gga ttt gtt gtc aac atc gtc gaa gaa gcc agc gcc gac gtc gcc<br>Ala Gly Phe Val Val Asn Ile Val Glu Glu Ala Ser Ala Asp Val Ala<br>370                           375                       380               385 | 1748 |
| gaa ggc ctc gtc atc cga gca aac cca agc gtt gga tcc gaa atc cgc<br>Glu Gly Leu Val Ile Arg Ala Asn Pro Ser Val Gly Ser Glu Ile Arg<br>                    390                   395                    400 | 1796 |
| caa ggg gcc acc gtc acc atc acc gtg tcc acc ggc cga gaa atg atc<br>Gln Gly Ala Thr Val Thr Ile Thr Val Ser Thr Gly Arg Glu Met Ile<br>                    405                     410                   415 | 1844 |
| aac atc cca gac gtc tcc ggc atg aca ctt gag gac gcc gcc cgc gcc<br>Asn Ile Pro Asp Val Ser Gly Met Thr Leu Glu Asp Ala Ala Arg Ala<br>                420                     425                     430 | 1892 |
| ctc gaa gac gtt ggt ctc ata ctc aac caa aac gtt cgg gaa gaa acc<br>Leu Glu Asp Val Gly Leu Ile Leu Asn Gln Asn Val Arg Glu Glu Thr<br>435                           440                       445 | 1940 |
| tcc gac gac gtc gaa tct ggc ctc gtc atc gac caa aac ccc gaa gcc<br>Ser Asp Asp Val Glu Ser Gly Leu Val Ile Asp Gln Asn Pro Glu Ala<br>450                           455                     460               465 | 1988 |
| ggc caa gaa gta gtc gtg ggt tcc tct gta tct cta acc atg tct tca<br>Gly Gln Glu Val Val Val Gly Ser Ser Val Ser Leu Thr Met Ser Ser<br>                    470                   475                    480 | 2036 |
| ggc acc gag agc atc cga gtg ccc aac ctc acc ggc atg aac tgg tca<br>Gly Thr Glu Ser Ile Arg Val Pro Asn Leu Thr Gly Met Asn Trp Ser | 2084 |

-continued

```
                485                 490                 495
caa gca gaa caa aac ctc atc tcc atg ggc ttt aac ccc aca gct tcc        2132
Gln Ala Glu Gln Asn Leu Ile Ser Met Gly Phe Asn Pro Thr Ala Ser
        500                 505                 510 tac tta gac agc agc gaa cca gaa ggc gaa gtc ctc tca gtt tcc agc        2180
Tyr Leu Asp Ser Ser Glu Pro Glu Gly Glu Val Leu Ser Val Ser Ser
    515                 520                 525 caa gga act gaa cta ccc aag ggt tca tcc atc aca gtg gaa gtc tcc        2228
Gln Gly Thr Glu Leu Pro Lys Gly Ser Ser Ile Thr Val Glu Val Ser
530                 535                 540                 545 aac ggc atg ctc atc caa gcc ccc gat ctc gcc cgc atg tcc acc gaa        2276
Asn Gly Met Leu Ile Gln Ala Pro Asp Leu Ala Arg Met Ser Thr Glu
                550                 555                 560 cag gcc atc agt gcc ctc cgc gct gct ggc tgg acc gcc cca gat caa        2324
Gln Ala Ile Ser Ala Leu Arg Ala Ala Gly Trp Thr Ala Pro Asp Gln
            565                 570                 575 tcc ctg atc gtc ggc gac tcc atc cac acc gca gcc ctc gtg gat caa        2372
Ser Leu Ile Val Gly Asp Ser Ile His Thr Ala Ala Leu Val Asp Gln
        580                 585                 590 aac aaa atc gga ttc caa tcc cca acc cct gca acc ctc ttc cgc aaa        2420
Asn Lys Ile Gly Phe Gln Ser Pro Thr Pro Ala Thr Leu Phe Arg Lys
    595                 600                 605 gac gcc caa gtg caa gtg cga ctc ttc gaa ttc gat ctc gct gca ctc        2468
Asp Ala Gln Val Gln Val Arg Leu Phe Glu Phe Asp Leu Ala Ala Leu
610                 615                 620                 625 gtg caa tagccaacaa ggaaaccgtc aaggtagctg cccggcaac tgatacgtta         2524
Val Gln agctcaaaca agataagtac cagttgctgg ggttttttcca agacaataaa ttatgaaggt    2584
gtgaacaatg ccaaaggcaa gagtaactaa aaacagagacc gcaccggttt caagcaaccc    2644
aagcgcaaac cgcaccccgg ttaagatcaa ttccgccgga accccaatgt ggtacaaggt    2704
catcatgttt gccttcatga tcgtcggcct agcctggttg atcattaact acctcgtggg    2764
cccacagatc ccattcatgg ctgatcttgg tgcatggaac tatggcatcg gcttcggtct    2824
gatgatcatc ggcctactca tgaccatggg ttggcgttaa tccttcaaaa a             2875
```

<210> SEQ ID NO 4
<211> LENGTH: 627
<212> TYPE: PRT
<213> ORGANISM: Corynebacterium glutamicum
<220> FEATURE:
<221> NAME/KEY: misc_feature
<222> LOCATION: (2343)..(2343)
<223> OTHER INFORMATION: C-T transition

<400> SEQUENCE: 4

```
Met Ser Glu Val Phe Ala Ala Thr Asp Thr Leu Ile Gly Arg Glu Val
1               5                   10                  15

Ala Val Lys Met Leu Arg Ile Asp Leu Ala Lys Asp Pro Asn Phe Arg
            20                  25                  30

Glu Arg Phe Arg Arg Glu Ala Gln Asn Ser Gly Arg Leu Ser His Ser
        35                  40                  45

Ser Ile Val Ala Val Phe Asp Thr Gly Glu Val Asp Lys Asp Gly Thr
    50                  55                  60

Ser Val Pro Tyr Ile Val Met Glu Arg Val Gln Gly Arg Asn Leu Arg
65                  70                  75                  80

Glu Val Val Thr Glu Asp Gly Val Phe Thr Pro Val Glu Ala Ala Asn
                85                  90                  95
```

-continued

```
Ile Leu Ile Pro Val Cys Glu Ala Leu Gln Ala Ser His Asp Ala Gly
            100                 105                 110

Ile Ile His Arg Asp Val Lys Pro Ala Asn Ile Met Ile Thr Asn Thr
        115                 120                 125

Gly Gly Val Lys Val Met Asp Phe Gly Ile Ala Arg Ala Val Asn Asp
    130                 135                 140

Ser Thr Ser Ala Met Thr Gln Thr Ser Ala Val Ile Gly Thr Ala Gln
145                 150                 155                 160

Tyr Leu Ser Pro Glu Gln Ala Arg Gly Lys Pro Ala Asp Ala Arg Ser
                165                 170                 175

Asp Ile Tyr Ala Thr Gly Cys Val Met Tyr Glu Leu Val Thr Gly Lys
            180                 185                 190

Pro Pro Phe Glu Gly Glu Ser Pro Phe Ala Val Ala Tyr Gln His Val
        195                 200                 205

Gln Glu Asp Pro Thr Pro Pro Ser Asp Phe Ile Ala Asp Leu Thr Pro
    210                 215                 220

Thr Ser Ala Val Asn Val Asp Ala Val Val Leu Thr Ala Met Ala Lys
225                 230                 235                 240

His Pro Ala Asp Arg Tyr Gln Thr Ala Ser Glu Met Ala Ala Asp Leu
                245                 250                 255

Gly Arg Leu Ser Arg Asn Ala Val Ser His Ala Ala Arg Ala His Val
            260                 265                 270

Glu Thr Glu Glu Thr Pro Glu Glu Pro Glu Thr Arg Phe Ser Thr Arg
        275                 280                 285

Thr Ser Thr Gln Val Ala Pro Ala Ala Gly Val Ala Ala Ser Thr
    290                 295                 300

Gly Ser Gly Ser Ser Arg Lys Arg Gly Ser Arg Gly Leu Thr Ala
305                 310                 315                 320

Leu Ala Ile Val Leu Ser Leu Gly Val Val Gly Val Ala Gly Ala Phe
                325                 330                 335

Thr Tyr Asp Tyr Phe Ala Asn Ser Ser Thr Ala Thr Ser Ala Ile
            340                 345                 350

Pro Asn Val Glu Gly Leu Pro Gln Gln Glu Ala Leu Thr Glu Leu Gln
        355                 360                 365

Ala Ala Gly Phe Val Val Asn Ile Val Glu Glu Ala Ser Ala Asp Val
    370                 375                 380

Ala Glu Gly Leu Val Ile Arg Ala Asn Pro Ser Val Gly Ser Glu Ile
385                 390                 395                 400

Arg Gln Gly Ala Thr Val Thr Ile Thr Val Ser Thr Gly Arg Glu Met
                405                 410                 415

Ile Asn Ile Pro Asp Val Ser Gly Met Thr Leu Glu Asp Ala Ala Arg
            420                 425                 430

Ala Leu Glu Asp Val Gly Leu Ile Leu Asn Gln Asn Val Arg Glu Glu
        435                 440                 445

Thr Ser Asp Asp Val Glu Ser Gly Leu Val Ile Asp Gln Asn Pro Glu
    450                 455                 460

Ala Gly Gln Glu Val Val Val Gly Ser Ser Val Ser Leu Thr Met Ser
465                 470                 475                 480

Ser Gly Thr Glu Ser Ile Arg Val Pro Asn Leu Thr Gly Met Asn Trp
                485                 490                 495

Ser Gln Ala Glu Gln Asn Leu Ile Ser Met Gly Phe Asn Pro Thr Ala
            500                 505                 510

Ser Tyr Leu Asp Ser Ser Glu Pro Glu Gly Glu Val Leu Ser Val Ser
```

-continued

```
              515                 520                    525
Ser Gln Gly Thr Glu Leu Pro Lys Gly Ser Ser Ile Thr Val Glu Val
        530                 535                 540

Ser Asn Gly Met Leu Ile Gln Ala Pro Asp Leu Ala Arg Met Ser Thr
545                     550                 555                 560

Glu Gln Ala Ile Ser Ala Leu Arg Ala Ala Gly Trp Thr Ala Pro Asp
                565                 570                 575

Gln Ser Leu Ile Val Gly Asp Ser Ile His Thr Ala Ala Leu Val Asp
                580                 585                 590

Gln Asn Lys Ile Gly Phe Gln Ser Pro Thr Pro Ala Thr Leu Phe Arg
            595                 600                 605

Lys Asp Ala Gln Val Gln Val Arg Leu Phe Glu Phe Asp Leu Ala Ala
        610                 615                 620

Leu Val Gln
625
```

NUCLEOTIDE SEQUENCES CODING FOR THE PKNB GENE

CROSS-REFERENCES TO RELATED APPLICATIONS

This application claims benefit to U.S. Provisional Application Ser. No. 60/297,250, filed on Jun. 12, 2001, and incorporated herein by reference.

BACKGROUND OF THE INVENTION

1. Field of the Invention

The present invention relates nucleotide sequences from corynebacteria coding for the pknB gene and a fermentation process for the preparation of amino acids using bacteria in which the endogenous pknB gene is amplified.

2. State of the Art

L-Amino acids, especially L-lysine, are used in human medicine, in the pharmaceutical industry, in the food industry, and, in particular, in animal nutrition. It is known that amino acids are prepared by the fermentation of strains of corynebacteria, especially *Corynebacterium glutamicum*. Because of their great importance, attempts are constantly being made to improve these preparative processes. Improvements to the processes may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains which are resistant to antimetabolites or auxotrophic for metabolites important in regulation, and produce amino acids.

Methods of recombinant DNA technology have also been used for some years to improve L-amino acid-producing strains of *Corynebacterium* by amplifying individual amino acid biosynthesis genes and studying the effect on amino acid production. However, there remains a need for improved methods of producing L-amino acids.

SUMMARY OF THE INVENTION

It is an object of the present invention to provide novel measures for improving the preparation of amino acids by fermentation.

It is another object of the present invention to provide nucleic acid sequences which are useful for the production of amino acids.

Accordingly, the present invention provides an isolated polynucleotide from *corynebacteria* which contains a polynucleotide sequence coding for the pknB gene and is selected from the following group:

(a) a polynucleotide which is at least 70% identical to a polynucleotide coding for a polypeptide containing the amino acid sequence of SEQ ID No. 2, (b) a polynucleotide coding for a polypeptide containing an amino acid sequence which is at least 70% identical to the amino acid sequence of SEQ ID No. 2, (c) a polynucleotide which is complementary to the polynucleotides of (a) or (b), and (d) a polynucleotide containing at least 15 consecutive nucleotides of the polynucleotide sequence of (a), (b) or (c), where the polypeptide preferably has the activity of protein kinase B.

The present invention also provides the above-mentioned polynucleotide, which is preferably a replicatable DNA containing:

(i) the nucleotide sequence shown in SEQ ID No. 1, or (ii) at least one sequence corresponding to sequence (i) within the degeneracy of the genetic code, or (iii) at least one sequence which hybridizes with the sequence complementary to sequence (i) or (ii), and optionally (iv) neutral sense mutations in (i).

The present invention also provides:

a replicatable polynucleotide, especially DNA, containing the nucleotide sequence as shown in SEQ ID No. 1, a polynucleotide coding for a polypeptide containing the amino acid sequence as shown in SEQ ID No. 2, a vector containing the polynucleotide according to the invention, especially a shuttle vector or plasmid vector, and corynebacteria which contain the vector or in which the endogeny pknB gene is amplified.

The present invention also provides a fermentation process for the preparation of an L-amino acid, comprising:

(a) fermenting corynebacteria which produce the L-amino acid in a medium, wherein at least the pknB gene or nucleotide sequences coding therefor are amplified in the corynebacteria, (b) enriching the L-amino acid in the medium or in the cells of the corynebacteria, and (c) isolating the L-amino acid.

The present invention additionally provides polynucleotides consisting substantially of a polynucleotide sequence which are obtainable by screening, by means of hybridization, of an appropriate gene library of a *corynebacterium*, containing the complete gene or parts thereof, with a probe containing the sequence of the polynucleotide of the invention according to SEQ ID No. 1 or a fragment thereof, and by isolation of the polynucleotide sequence.

A more complete appreciation of the invention and many of the attendant advantages thereof will be readily obtained as the same becomes better understood by reference to the following detailed description.

DETAILED DESCRIPTION OF THE INVENTION

When L-amino acids or amino acids are mentioned hereafter, this is understood to refer to one or more amino acids, including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine is mentioned hereafter, this is understood to refer to not only the bases but also the salts, e.g. lysine monohydrochloride or lysine sulfate.

As hybridization probes for RNA, cDNA and DNA, polynucleotides containing the sequences according to the invention are suitable for isolating the full length of nucleic acids, or polynucleotides or genes, coding for protein kinase B, or for isolating nucleic acids, or polynucleotides or genes, whose sequence exhibits a high degree of similarity to the sequence of the pknB gene. They are also suitable for incorporation into so-called arrays, micro-arrays or DNA chips for detecting and determining the corresponding polynucleotides.

Polynucleotides containing the sequences according to the invention are further suitable as primers for the preparation, by the polymerase chain reaction (PCR), of DNA of genes coding for protein kinase B.

Such oligonucleotides serving as probes or primers contain at least 25, 26, 27, 28, 29 or 30, preferably at least 20, 21, 22, 23 or 24 and very particularly preferably at least 15, 16, 17, 18 or 19 consecutive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides are also suitable.

As used herein, the term "isolated" refers to a material, e.g., a nucleic acid sequence, separated from its natural environment.

"Polynucleotide" refers in general to polyribonucleotides and polydeoxyribonucleotides, it being possible for the RNAs or DNAs in question to be unmodified or modified.

The polynucleotides according to the invention include a polynucleotide according to SEQ ID No. 1 or a fragment prepared therefrom, as well as polynucleotides which are in particular at least 70% to 80%, preferably at least 81% to 85%, particularly preferably at least 86% to 90% and very particularly preferably at least 91%, 93%, 95%, 97% or 99% identical to the polynucleotide according to SEQ ID No. 1 or a fragment prepared therefrom.

"Polypeptides" are understood as meaning peptides or proteins containing two or more amino acids bonded via peptide links.

The polypeptides according to the invention include a polypeptide according to SEQ ID No. 2, especially those with the biological activity of protein kinase B and also those which are at least 70% to 80%, preferably at least 81% to 85%, particularly preferably at least 86% to 90% and very particularly preferably at least 91%, 93%, 95%, 97% or 99% identical to the polypeptide according to SEQ ID No. 2, and having the activity of protein kinase B.

The invention further relates to a fermentation process for the preparation of amino acids selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using corynebacteria which, in particular, already produce amino acids and in which the nucleotide sequences coding for the pknB gene are amplified and, in particular, overexpressed.

In this context the term "enhancement" describes the increase in the intracellular activity, in a microorganism, of one or more enzymes which are coded for by the appropriate DNA, for example by increasing the copy number of the gene(s) or allele(s), using a strong promoter or using a gene or allele coding for an appropriate enzyme with a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms provided by the present invention can produce L-amino acids from glucose, sucrose, lactose, fructose, maltose, molasses, starch or cellulose or from glycerol and ethanol. The microorganisms can be representatives of corynebacteria, especially of the genus Corynebacterium. The species Corynebacterium glutamicum may be mentioned in particular in the genus Corynebacterium, which is known to those skilled in the art for its ability to produce L-amino acids.

The following known wild-type strains:
Corynebacterium glutamicum ATCC13032
Corynebacterium acetoglutamicum ATCC15806
Corynebacterium acetoacidophilum ATCC13870
Corynebacterium thermoaminogenes FERM BP-1539
Corynebacterium melassecola ATCC17965
Brevibacterium flavum ATCC14067
Brevibacterium lactofermentum ATCC13869 and
Brevibacterium divaricatum ATCC14020 and L-amino acid-producing mutants or strains prepared therefrom, are particularly suitable strains of the genus Corynebacterium, especially of the species Corynebacterium glutamicum (C. glutamicum).

The novel pknB gene of C. glutamicum coding for the enzyme protein kinase B (EC 2.7.1.37) has been isolated using the procedures described herein.

The first step in isolating the pknB gene or other genes of C. glutamicum is to construct a gene library of this microorganism in Escherichia coli (E. coli). The construction of gene libraries is documented in generally well-known textbooks and manuals. Examples which may be mentioned are the textbook by Winnacker entitled From Genes to Clones, Introduction to Gene Technology (Verlag Chemie, Weinheim, Germany, 1990) or the manual by Sambrook et al. entitled Molecular Cloning, A Laboratory Manual (Cold Spring Harbor Laboratory Press, 1989). A very well-known gene library is that of the E. coli K-12 strain W3110, which was constructed by Kohara et al. (Cell 50, 495–508 (1987)) in λ vectors. Bathe et al. (Molecular and General Genetics 252, 255–265, 1996) describe a gene library of C. glutamicum ATCC13032, which was constructed using cosmid vector SuperCos I (Wahl et al., 1987, Proceedings of the National Academy of Sciences USA 84, 2160–2164) in the E. coli K-12 strain NM554 (Raleigh et al., 1988, Nucleic Acids Research 16, 1563–1575). Börmann et al. (Molecular Microbiology 6(3), 317–326 (1992)) in turn describe a gene library of C. glutamicum ATCC13032 using cosmid pHC79 (Hohn and Collins, Gene 11, 291–298 (1980)).

A gene library of C. glutamicum in E. coli can also be constructed using plasmids like pBR322 (Bolivar, Life Sciences 25, 807–818 (1979)) or pUC9 (Vieira et al., 1982, Gene 19, 259–268). Restriction- and recombination-defective E. coli strains are particularly suitable as hosts, an example being the strain DH5αmcr, which has been described by Grant et al. (Proceedings of the National Academy of Sciences USA 87 (1990) 4645–4649). The long DNA fragments cloned with the aid of cosmids can then in turn be subcloned into common vectors suitable for sequencing, and subsequently sequenced, e.g. as described by Sanger et al. (Proceedings of the National Academy of Sciences of the United States of America 74, 5463–5467, 1977).

The DNA sequences obtained can then be examined with known algorithms or sequence analysis programs, e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The novel DNA sequence of C. glutamicum coding for the pknB gene was found and, as SEQ ID No. 1, forms part of the present invention. Furthermore, the amino acid sequence of the corresponding protein was derived from the DNA sequence by the methods described above. The resulting amino acid sequence of the pknB gene product is shown in SEQ ID No. 2.

Coding DNA sequences which result from SEQ ID No. 1 due to the degeneracy of the genetic code also within the scope of the present invention. Likewise, DNA sequences which hybridize with SEQ ID No. 1 or portions of SEQ ID No. 1 form part of the invention. Furthermore, conservative amino acid exchanges, e.g. the exchange of glycine for alanine or of aspartic acid for glutamic acid in proteins, are known to those skilled in the art as "sense mutations", which do not cause a fundamental change in the activity of the protein, i.e. they are neutral. It is also known that changes at the N- and/or C-terminus of a protein do not substantially impair its function or may even stabilize it. Those skilled in the art will find information on this subject in Ben-Bassat et al. (Journal of Bacteriology 169, 751–757 (1987)), O'Regan et al. (Gene 77, 237–251 (1989)), Sahin-Toth et al. (Protein Sciences 3, 240–247 (1994)) and Hochuli et al. (Bio/Technology 6, 1321–1325 (1988)), inter alia, and in well-known textbooks on genetics and molecular biology. Amino acid sequences which correspondingly result from SEQ ID No. 2 also form part of the invention.

Likewise, DNA sequences which hybridize with SEQ ID No. 1 or portions of SEQ ID No. 1 are within the scope of the present invention. Finally, DNA sequences which are prepared by the polymerase chain reaction (PCR) using primers resulting from SEQ ID No. 1 form part of the invention. Such oligonucleotides typically have a length of at least 15 nucleotides.

Those skilled in the art can find instructions on the identification of DNA sequences by means of hybridization in the manual entitled "The DIG System User's Guide for Filter Hybridization" from Boehringer Mannheim GmbH (Mannheim, Germany, 1993) and in Liebl et al. (International Journal of Systematic Bacteriology (1991) 41, 255–260), inter alia. Hybridization takes place under stringent conditions; in other words, only hybrids for which the probe and the target sequence, i.e. the polynucleotides treated with the probe, are at least 70% identical are formed. It is known that the stringency of hybridization, including the washing steps, is influenced or determined by varying the buffer composition, the temperature and the salt concentration. The hybridization reaction is preferably carried out under relatively low stringency compared with the washing steps (Hybaid Hybridisation Guide, Hybaid Limited, Teddington, UK, 1996).

The hybridization reaction can be carried out for example using a 5×SSC buffer at a temperature of approx. 50° C.–68° C., it also being possible for probes to hybridize with polynucleotides which are less than 70% identical to the sequence of the probe. Such hybrids are less stable and are removed by washing under stringent conditions. This can be achieved for example by lowering the salt concentration to 2×SSC and subsequently to 0.5×SSC if necessary (The DIG System User's Guide for Filter Hybridization, Boehringer Mannheim, Mannheim, Germany, 1995), the temperature being adjusted to approx. 50° C.–68° C. It is possible to lower the salt concentration to 0.1×SSC if necessary. By raising the hybridization temperature in approx. 1–2° C. steps from 50° C. to 68° C., it is possible to isolate polynucleotide fragments which are e.g. at least 70%, at least 80% or at least 90% to 95% identical to the sequence of the probe used. Further instructions on hybridization are commercially available in the form of kits (e.g. DIG Easy Hyb from Roche Diagnostics GmbH, Mannheim, Germany, Catalog No. 1603558).

Those skilled in the art can find instructions on the amplification of DNA sequences with the aid of the polymerase chain reaction (PCR) in the manual by Gait entitled Oligonucleotide Synthesis: A Practical Approach (IRL Press, Oxford, UK, 1984) and in Newton and Graham: PCR (Spektrum Akademischer Verlag, Heidelberg, Germany, 1994), inter alia.

It has been found that, after overexpression of the pknB gene, the production of amino acids by corynebacteria is improved.

Overexpression can be achieved by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase the expression in the course of the production of amino acid by fermentation. Measures for prolonging the life of the mRNA also improve the expression. Furthermore, the enzyme activity is also enhanced by preventing the degradation of the enzyme protein. The genes or gene constructs can either be located in plasmids of variable copy number or integrated and amplified in the chromosome. Alternatively, it is also possible to achieve overexpression of the genes in question by changing the composition of the media and the culture technique.

Those skilled in the art can find relevant instructions in Martin et al. (Bio/Technology 5, 137–146 (1987)), Guerrero et al. (Gene 138, 35–41 (1994)), Tsuchiya and Morinaga (Bio/Technology 6, 428–430 (1988)), Eikmanns et al. (Gene 102, 93–98 (1991)), EP 0 472 869, U.S. Pat. No. 4,601,893, Schwarzer and Pühler (Bio/Technology 9, 84–87 (1991)), Reinscheid et al. (Applied and Environmental Microbiology 60, 126–132 (1994)), LaBarre et al. (Journal of Bacteriology 175, 1001–1007 (1993)), WO 96/15246, Malumbres et al. (Gene 134, 15–24 (1993)), JP-A-10-229891, Jensen and Hammer (Biotechnology and Bioengineering 58, 191–195 (1998)) and Makrides (Microbiological Reviews 60, 512–538 (1996)), inter alia, and in well-known textbooks on genetics and molecular biology.

For amplification, the pknB gene according to the invention has been overexpressed for example with the aid of episomal plasmids. Suitable plasmids are those which are replicated in corynebacteria. Numerous known plasmid vectors, e.g. pZ1 (Menkel et al., Applied and Environmental Microbiology (1989) 64, 549–554), pEKEx1 (Eikmanns et al., Gene 102, 93–98 (1991)) or pHS2-1 (Sonnen et al., Gene 107, 69–74 (1991)), are based on cryptic plasmids pHM1519, pBL1 or pGA1. Other plasmid vectors, e.g. those based on pCG4 (U.S. Pat. No. 4,489,160), pNG2 (Serwold-Davis et al., FEMS Microbiology Letters 66, 119–124 (1990)) or pAG1 (U.S. Pat. No. 5,158,891), can be used in the same way.

Other suitable plasmid vectors are those which make it possible to use the gene amplification process by integration into the chromosome, as described for example by Reinscheid et al. (Applied and Environmental Microbiology 60, 126–132 (1994)) for the duplication or amplification of the hom-thrB operon. In this method the complete gene is cloned into a plasmid vector which can replicate in a host (typically E. coli), but not in C. glutamicum. Examples of suitable vectors are pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994), Journal of Biological Chemistry 269, 32678–84; U.S. Pat. No. 5,487,993), pCR®Blunt (Invitrogen, Groningen, The Netherlands; Bernard et al., Journal of Molecular Biology 234, 534–541 (1993)), pEM1 (Schrumpf et al., 1991, Journal of Bacteriology 173, 4510–4516) or pBGS8 (Spratt et al., 1986, Gene 41, 337–342). The plasmid vector containing the gene to be amplified is then transferred to the desired strain of *C. glutamicum* by conjugation or transformation. The method of conjugation is described for example in Schäfer et al. (Applied and Environmental Microbiology 60, 756–759 (1994)). Methods of transformation are described for example in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a crossover event, the resulting strain contains at least two copies of the gene in question.

It has also been found that amino acid exchanges in the section between position 581 and position 587 of the amino acid sequence of protein kinase B, shown in SEQ ID No. 2, improve the production of amino acids, especially lysine, by corynebacteria. Preferably, L-proline in position 584 is exchanged for any other proteogenic amino acid except L-proline, preferably for L-serine or L-threonine and very particularly preferably for L-serine.

SEQ ID No. 3 shows the base sequence of the pknB-1547 allele contained in the strain DM1547. The pknB-1547 allele codes for a protein whose amino acid sequence is shown in SEQ ID No. 4. The protein contains L-serine in position 584. The DNA sequence of the pknB-1547 allele (SEQ ID No. 3) contains the base thymine in place of the base cytosine contained in the pknB wild-type gene (SEQ ID No. 1) in position 2343.

Mutagenesis can be carried out by conventional methods using mutagenic substances such as N-methyl-N'-nitro-N-nitrosoguanidine or ultraviolet light. Mutagenesis can also be carried out using in vitro methods such as treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger (Gene Technology for Beginners), Spektrum Akademischer Verlag, Heidelberg, 1993), or the polymerase chain reaction (PCR) as described in the manual by Newton and Graham (PCR, Spektrum Akademischer Verlag, Heidelberg, 1994).

The corresponding alleles or mutations are sequenced and introduced into the chromosome by the method of gene replacement, for example as described in Peters-Wendisch et al. (Microbiology 144, 915–927 (1998)) for the pyc gene of *C. glutamicum*, in Schäfer et al. (Gene 145, 69–73 (1994)) for the hom-thrB gene region of *C. glutamicum* or in Schäfer et al. (Journal of Bacteriology 176, 7309–7319 (1994)) for the cg1 gene region of *C. glutamicum*. The corresponding alleles or the associated proteins can optionally be amplified in turn.

In addition it can be advantageous for the production of L-amino acids to amplify and, in particular, overexpress not only the pknB gene but also one or more enzymes of the particular biosynthetic pathway, the glycolysis, the anaplerosis, the citric acid cycle, the pentose phosphate cycle or the amino acid export, and optionally regulatory proteins.

Thus, for the production of L-amino acids, one or more genes selected from the following group can be amplified and, in particular, overexpressed in addition to amplification of the endogene pknB gene:

the dapA gene coding for dihydrodipicolinate synthase (EP-B-0 197 335), the gap gene coding for glyceraldehyde 3-phosphate dehydrogenase (Eikmanns (1992), Journal of Bacteriology 174, 6076–6086), the tpi gene coding for triose phosphate isomerase (Eikmanns (1992), Journal of Bacteriology 174, 6076–6086), the pgk gene coding for 3-phosphoglycerate kinase (Eikmanns (1992), Journal of Bacteriology 174, 6076–6086), the zwf gene coding for glucose-6-phosphate dehydrogenase (JP-A-09224661), the pyc gene coding for pyruvate carboxylase (DE-A-198 31 609), the lysC gene coding for a feedback-resistant aspartate kinase (Accession no. P26512; EP-B-0387527; EP-A-0699759), the lysE gene coding for lysine export (DE-A-195 48 222), the hom gene coding for homoserine dehydrogenase (EP-A-0131171), the ilvA gene coding for threonine dehydratase (Möckel et al., Journal of Bacteriology (1992) 8065–8072) or the ilvA(Fbr) allele coding for a feedback-resistant threonine dehydratase (Möckel et al. (1994), Molecular Microbiology 13, 833–842), the ilvBN gene coding for acetohydroxy acid synthase (EP-B-0356739), the ilvD gene coding for dihydroxy acid dehydratase (Sahm and Eggeling (1999), Applied and Environmental Microbiology 65, 1973–1979), or the zwa1 gene coding for the Zwa1 protein (DE 199 59 328.0, DSM 13115).

In addition to amplification of the pknB gene, it can also be advantageous for the production of L-amino acids to attenuate one or more genes selected from the following group:

the pck gene coding for phosphoenol pyruvate carboxykinase (DE 199 50 409.1, DSM13047), the pgi gene coding for glucose-6-phosphate isomerase (U.S. Ser. No. 09/396,478, DSM12969), the poxB gene coding for pyruvate oxidase (DE 199 51 975.7, DSM13114), or the zwa2 gene coding for the Zwa2 protein (DE 199 59 327.2, DSM13113), and, in particular, to reduce the expression.

In this context the term "attenuation" describes the reduction or switching-off of the intracellular activity, in a microorganism, of one or more enzymes (proteins) which are coded for by the appropriate DNA, for example by using a weak promoter or using a gene or allele coding for an appropriate enzyme with a low activity, or inactivating the appropriate gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

It can also be advantageous for the production of amino acids not only to overexpress the pknB gene but also to switch off unwanted secondary reactions (Nakayama:

"Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention are also provided by the invention and can be cultivated for the production of amino acids continuously or discontinuously by the batch process, the fed batch process or the repeated fed batch process. A summary of known cultivation methods is described in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular strains. Descriptions of culture media for various microorganisms can be found in "Manual of Methods for General Bacteriology" of the American Society for Bacteriology (Washington D.C., USA, 1981).

Carbon sources which can be used are sugars and carbohydrates, e.g. glucose, sucrose, lactose, fructose, maltose, molasses, starch and cellulose, oils and fats, e.g. soybean oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture.

Nitrogen sources which can be used are organic nitrogen-containing compounds such as peptones, yeast extract, meat extract, malt extract, corn steep liquor, soybean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are phosphoric acid, potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Suitable precursors can also be added to the culture medium. The feed materials can be added to the culture all at once or fed in appropriately during cultivation.

The pH of the culture is controlled by the appropriate use of basic compounds such as sodium hydroxide, potassium hydroxide, ammonia or aqueous ammonia, or acidic compounds such as phosphoric acid or sulfuric acid. Foaming can be controlled using antifoams such as fatty acid polyglycol esters. The stability of plasmids can be maintained by adding suitable selectively acting substances, e.g. antibiotics, to the medium. Aerobic conditions are maintained by introducing oxygen or oxygen-containing gaseous mixtures, e.g. air, into the culture. The temperature of the culture is normally 20° C. to 45° C. and preferably 25° C. to 40° C. The culture is continued until the formation of the desired product has reached a maximum. This objective is normally achieved within 10 hours to 160 hours.

Methods of determining L-amino acids are well-known to those skilled in the art. They can be analyzed for example by ion exchange chromatography with subsequent ninhydrin derivation, as described by Spackman et al. (Analytical Chemistry 30 (1958) 1190), or by reversed phase HPLC, as described by Lindroth et al. (Analytical Chemistry (1979) 51, 1167–1174).

A pure culture of the *Corynebacterium glutamicum* strain DM1547 was deposited as DSM13994 in the Deutsche Sammlung für Mikroorganismen und Zellkulturen (German Collection of Microorganisms and Cell Cultures (DSMZ), Brunswick, Germany) on 16 Jan. 2001 under the terms of the Budapest Treaty.

The fermentation process according to the invention is used for the preparation of amino acids.

Another aspect of the present invention is a method of identifying nucleic acids which code for protein kinase B or have a high degree of similarity to the sequence of the pknB gene, comprising:

contacting a sample with the polynucleotide of claim 1 under conditions suitable for the polynucleotide to hybridize to another nucleic acid which codes for protein kinase B or have a high degree of similarity to the sequence of the pknB gene. In one embodiment, the another nucleic acid referred to above is RNA, cDNA, or DNA. In another embodiment, the method is conducted on an array, micro-array, or DNA chip.

EXAMPLES

Having generally described this invention, a further understanding can be obtained by reference to certain specific examples which are provided herein for purposes of illustration only and are not intended to be limiting unless otherwise specified.

The isolation of plasmid DNA from *Escherichia coli* and all the techniques of restriction, Klenow treatment and alkaline phosphatase treatment were carried out according to Sambrook et al. (Molecular Cloning. A Laboratory Manual (1989), Cold Spring Harbor Laboratory Press, Cold Spring Harbor, N.Y., USA). Methods of transforming *Escherichia coli* are also described in this manual.

The composition of common nutrient media, such as LB or TY medium, can also be found in the manual by Sambrook et al.

Example 1

Preparation of a Genomic Cosmid Gene Library from *Corynebacterium glutamicum* ATCC13032

Chromosomal DNA from *Corynebacterium glutamicum* ATCC13032 was isolated as described in Tauch et al. (1995, Plasmid 33, 168–179) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Diagnostics GmbH, Mannheim, Germany, product description SAP, code no. 1758250). The DNA of cosmid vector SuperCos1 (Wahl et al. (1987), Proceedings of the National Academy of Sciences USA 84, 2160–2164), obtained from Stratagene (La Jolla, USA, product description SuperCos1 Cosmid Vector Kit, code no. 251301), was cleaved with the restriction enzyme XbaI (Amersham Pharmacia, Freiburg, Germany, product description XbaI, code no. 27-0948-02) and also dephosphorylated with shrimp alkaline phosphatase.

The cosmid DNA was then cleaved with the restriction enzyme BamHI (Amersham Pharmacia, Freiburg, Germany, product description BamHI, code no. 27-0868-04). The cosmid DNA treated in this way was mixed with the treated ATCC13032 DNA and the mixture was treated with T4 DNA ligase (Amersham Pharmacia, Freiburg, Germany, product description T4 DNA ligase, code no. 27-0870-04). The ligation mixture was then packaged into phages using Gigapack II XL Packing Extract (Stratagene, La Jolla, USA, product description Gigapack II XL Packing Extract, code no. 200217).

For infection of the *E. coli* strain NM554 (Raleigh et al., 1988, Nucleic Acid Research 16, 1563-1575), the cells were taken up in 10 mM $MgSO_4$ and mixed with an aliquot of the phage suspension. Infection and titering of the cosmid library were carried out as described in Sambrook et al. (1989, Molecular Cloning: A Laboratory Manual, Cold Spring Harbor), the cells being plated on LB agar (Lennox, 1955, Virology 1, 190) containing 100 mg/l of ampicillin. After incubation overnight at 37° C., recombinant single clones were selected.

Example 2

Isolation and Sequencing of the pknB Gene

The cosmid DNA of a single colony was isolated with the Qiaprep Spin Miniprep Kit (product no. 27106, Qiagen, Hilden, Germany) in accordance with the manufacturer's instructions and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Diagnostics GmbH, Mannheim, Germany, product description SAP, product no. 1758250). After separation by gel electrophoresis, the cosmid fragments in the size range from 1500 to 2000 bp were isolated with the QiaExII Gel Extraction Kit (product no. 20021, Qiagen, Hilden, Germany).

The DNA of sequencing vector pZero-1, obtained from Invitrogen (Groningen, The Netherlands, product description Zero Background Cloning Kit, product no. K2500-01), was cleaved with the restriction enzyme BamHI (Amersham Pharmacia, Freiburg, Germany, product description BamHI, product no. 27-0868-04). Ligation of the cosmid fragments into sequencing vector pZero-1 was carried out as described in Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then introduced into the *E. coli* strain DH5αMCR (Grant, 1990, Proceedings of the National Academy of Sciences USA 87, 4645–4649) by electroporation (Tauch et al. 1994, FEMS Microbiol. Letters 123, 343–7) and plated on LB agar (Lennox, 1955, Virology 1, 190) containing 50 mg/l of zeocin.

Plasmid preparation of the recombinant clones was carried out with Biorobot 9600 (product no. 900200, Qiagen, Hilden, Germany). Sequencing was carried out by the dideoxy chain termination method of Sanger et al. (1977, Proceedings of the National Academy of Sciences USA 74, 5463–5467) with modifications by Zimmermann et al. (1990, Nucleic Acids Research 18, 1067). The "RR dRhodamin Terminator Cycle Sequencing Kit" from PE Applied Biosystems (product no. 403044, Weiterstadt, Germany) was used. Separation by gel electrophoresis and analysis of the sequencing reaction were carried out in a "Rotiphorese NF acrylamide/bisacrylamide" gel (29:1) (product no. A124.1, Roth, Karlsruhe, Germany) with the "ABI Prism 377" sequencer from PE Applied Biosystems (Weiterstadt, Germany).

The raw sequence data obtained were then processed using the Staden programming package (1986, Nucleic Acids Research 14, 217–231), version 97-0. The individual sequences of the pZero-1 derivatives were assembled into a cohesive contig. Computer-assisted coding region analysis was performed with the XNIP program (Staden, 1986, Nucleic Acids Research 14, 217–231).

The nucleotide sequence obtained is shown in SEQ ID No. 1. Analysis of the nucleotide sequence gave an open reading frame of 1884 base pairs, which was called the pknB gene. The pknB gene codes for a protein of 627 amino acids.

Obviously, numerous modifications and variations of the present invention are possible in light of the above teachings. It is therefore to be understood that within the scope of the appended claims, the invention may be practiced otherwise than as specifically described herein.

All of the publications cited above are incorporated herein by reference.

This application is based, inter alia, on German Patent Application Serial No. 100 44 912.3, filed on Sep. 12, 2000; and German Patent Application Serial No. 101 20 095.1, filed on Apr. 25, 2001, both of which are incorporated herein by reference.

What is claimed is:

1. An isolated polynucleotide consisting of at least 26 consecutive nucleotides of SEQ ID NO:1 or the full complement of SEQ ID NO:1, wherein the isolated polynucleotide has the function of a probe in a hybridization reaction to isolate or identify a polynucleotide encoding a protein comprising the amino acid sequence of SEQ ID NO:2.

2. A vector comprising the isolated polynucleotide of claim 1.

3. A method of identifying a nucleic acid which is at least 90% identical to the polynucleotide of SEQ ID NO:1 and which encodes a protein having protein kinase B activity, comprising contacting a sample with a probe consisting of at least 26 consecutive nucleotides of SEQ ID NO:1 under conditions suitable for the nucleic acid to hybridize to the probe; and determining whether the nucleic acid is at least 90% identical to the polynucleotide of SEQ ID NO:1 and encodes a polypeptide having protein kinase B activity.

4. An isolated polynucleotide consisting of at least 32 or 35 consecutive nucleotides of SEQ ID NO:1 or the full complement of SEQ ID NO:1, wherein the isolated polynucleotide has the function of a probe in a hybridization reaction to isolate or identify a polynucleotide encoding a protein comprising the amino acid sequence of SEQ ID NO:2.

* * * * *